United States Patent [19]

Matsunaga et al.

[11] Patent Number: 4,985,412
[45] Date of Patent: Jan. 15, 1991

[54] PHOSPHORIC ACID ESTER, PROCESS FOR PREPARING THE SAME, AND DETERGENT COMPOSITION CONTAINING THE SAME

[75] Inventors: Akira Matsunaga, Wakayama; Junya Wakatsuki, Utsunomiya; Nobutaka Horinishi; Takashi Imamura, both of Wakayama; Tomihiro Kurosaki, Ennan, all of Japan

[73] Assignee: Kao Corporation, Tokyo, Japan

[21] Appl. No.: 260,868

[22] Filed: Oct. 21, 1988

[30] Foreign Application Priority Data

Oct. 21, 1987 [JP] Japan ................. 62-265989

[51] Int. Cl.$^5$ ............................ C07F 9/09; C07F 9/10
[52] U.S. Cl. ........................... 514/70; 252/105; 252/328; 558/169
[58] Field of Search .................. 558/169; 514/70; 252/105, 528

[56] References Cited

U.S. PATENT DOCUMENTS 3,304,349  2/1967  Shen ................................ 558/169
4,623,743  11/1986 Kurosaki et al. ................. 558/169

FOREIGN PATENT DOCUMENTS 2020289  11/1979  United Kingdom .

OTHER PUBLICATIONS

Dewert 78-46349A/26 (46349A).
Derwent 79-53543B/29 (53543B).
Dewent 79-91917B/51 (91917B).
Patent Abstract of Japanese JP62-149690 (1987).

*Primary Examiner*—Mark L. Berch
*Attorney, Agent, or Firm*—Oblon, Spivak, McClelland, Maier & Neustadt

[57] ABSTRACT

Phosphoric acid esters represented by the following formulae (I) and (IX) as well as processes for preparing them are disclosed.

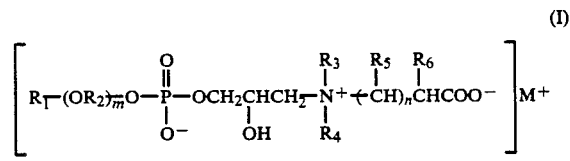

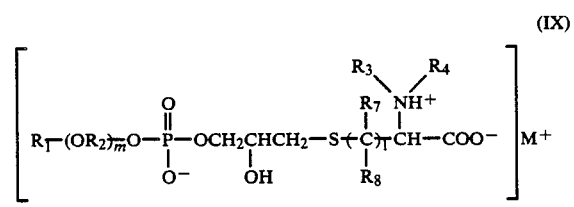

wherein $R_1$ represents a linear or branched, alkyl or alkenyl group having a $C_{1-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content, $R_3$ and $R_4$ independently denote a hydrogen atom or an alkyl group having a $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s), excepting for a mercapto group, $R_7$ and $R_8$ independently denote a hydrogen atom, or an alkyl, or alkenyl group, m is an integer of 0-30, n is an integer of 0-5, l is an integer of 0-3, M is a hydrogen atom, an alkali metal, an alkali earth metal, on ammonium group, an alkyl amine group, or an alkanol amine group. The phosphoric acid ester have outstanding surface activity and good foaming capability, and imparts only extremely low irritation to the skin. The detergent composition into which they are formulated is particularly useful as, shampoo, baby shampoo, body shampoo.

3 Claims, 2 Drawing Sheets

PHOSPHORIC ACID ESTER, PROCESS FOR PREPARING THE SAME, AND DETERGENT COMPOSITION CONTAINING THE SAME

BACKGROUND OF THE INVENTION

1. Field of the Invention:

This invention relates to a novel phosphoric acid ester and a novel detergent composition, and, more particularly, to a phosphoric acid ester represented by the following formula (I):

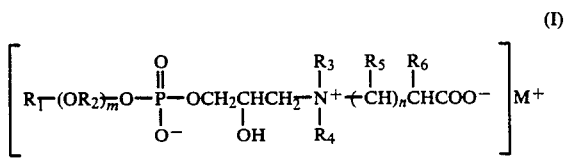

wherein $R_1$ represents a linear or branched alkyl or alkenyl group having a $C_{1-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content, $R_3$ and $R_4$ independently denote a hydrogen atom or an alkyl group having a $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s), excepting for a mercapto group, m is an integer of 0–30, n is an integer of 0–5, M is a hydrogen atom, an alkali metal, an alkali earth metal, an ammonium group, an alkyl amine group, or an alkanol amine group. The invention also relates to a a phosphoric acid ester represented by the following formula (IX):

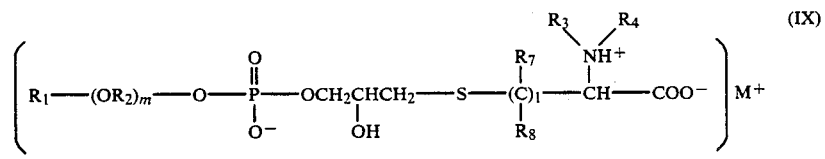

wherein $R_7$ and $R_8$ independently denote a hydrogen atom, or an alkyl or alkenyl group, and l is an integer of 0–3, and $R_1$, $R_2$, $R_3$, $R_4$, m, and M have the same meanings as defined above. The invention also is directed to processes for preparing the above phosphoric acid esters, as well as detergent compositions comprising the same.

Description of the Background

Phosphoric acid esters are used in wide varieties of fields as detergents, fiber treating agents, emulsifiers, rust inhibitors, liquid ion-exchangers, medicines, or the like.

Among surface active agents currently used as detergents, alkyl sulfates, alkylbenzene sulfonates, α-olefin sulfonates, and the like tend to make the skin roughened. Because of this, the use of less irritative surface active agents such as phosphoric acid monoesters, acyl glutamates, and the like are attracting a wider popularity.

The rise in the standard of living in recent years, however, demands the development of cosmetics and toiletries which can provide a higher safety and more sophisticated functions to human bodies.

Many types of phosphoric acid ester-type compounds having a quaternary ammonium salt in the molecule, which are called phospholipids, including lecithin, phosphatidyl serine, and the like, are present in living bodies. These phospholipids are widely used because of their surface-active, emulsifying, and physiological characteristics. Compounds having molecular structures analogous to these phospholipids can be presumed to be less irritative to living bodies than monoalkyl phosphate salts. Because of this, many kinds of phospholipid analogous compounds are synthesized. Many of the phospholipid analogous compounds, however, require a multiple steps of reactions for their synthesis, and therefore most of them could be synthesized only at a poor yield [For instance, E. Baer et al., J. Amer. Chem. Soc., 72, 942 (1950) and T. Yamakawa, Lipids, Kyoritsu Publishing Co. (1973)]. In addition, quite a few of them require compounds as raw materials which are difficult to synthesize or involve difficulties in separating the target compounds after the reaction, resulting in a poor production yield. Furthermore, many of the compounds exhibit only insufficient surface activity (For example, Japanese Patent Publication No. 23330/1967, Japanese Patent Publication No. 1654/1973, and U.S. Pat. No. 3,507,937).

In view of this situation, the present inventors have undertaken extensive studies to resolve above problems, and as a result have found that the novel phosphoric acid esters represented by formulae (I) and (IX) can be prepared through a simple process at a high purity and high yield using raw materials which are inexpensive and readily available. The inventors have further found that the novel phosphoric acid esters represented by formulae (I) and (IX) are less irritative to the skin and hair, and exhibits excellent foaming and detergent capabilities. These findings have led to the completion of this invention.

SUMMARY OF THE INVENTION

Accordingly, an object of this invention is to provide a novel phosphoric acid ester represented by the following formula (I):

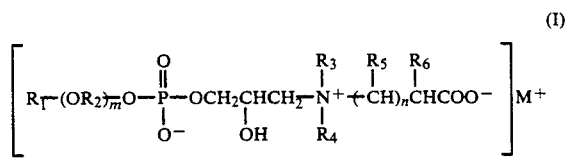

wherein $R_1$ represents a linear or branched, alkyl or alkenyl group having a $C_{1-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content, $R_3$ and $R_4$ independently denote a hydrogen atom or an alkyl group having a $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s), excepting for a mercapto group, m is an integer of 0–30, n is an integer of 0–5, M is a hydrogen atom, an alkali metal, an alkali earth metal, an ammonium group, an alkyl amine group, or an alkanol amine group.

Another object of the invention is to provide a phosphoric acid ester represented by the following formula (IX):

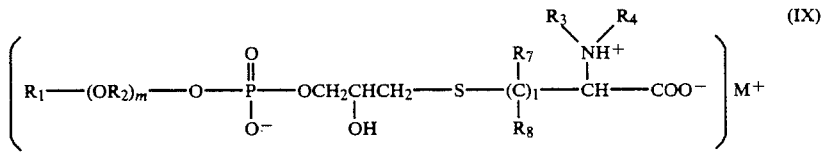

wherein $R_7$ and $R_8$ independently denote a hydrogen atom, or an alkyl or alkenyl group, and l is an integer of 0–3, and $R_1$, $R_2$, $R_3$, $R_4$, m, and M have the same meanings as defined above.

Still another object is to provide processes for the preparation of phosphoric acid esters represented by the above formulae (I) and (IX).

It is also an object of this invention to provide detergent compositions comprising phosphoric acid ester represented by the above formulae (I) or (IX).

Other objects, features and advantages of the invention will hereinafter become more readily apparent from the following description.

DETAILED DESCRIPTION OF THE INVENTION AND PREFERRED EMBODIMENTS

Figure 1:
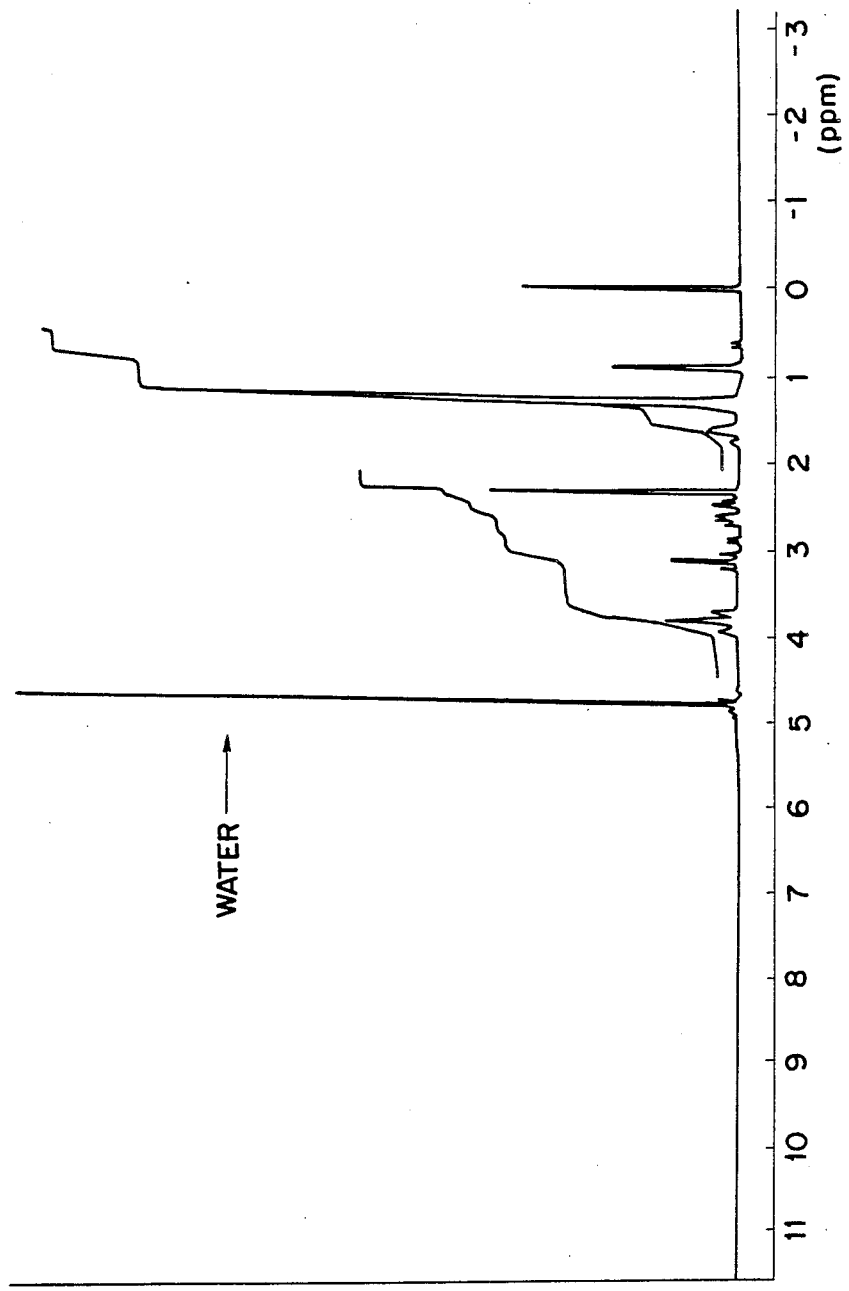
FIG. 1 is a drawing showing $^1$H-NMR Spectrum of sodium dodecyl 2-hydroxy-3-N-carboxymethyl-N-methylammoniopropyl phosphate prepared in Example 1.

Enumerated as examples of a linear or branched, alkyl or alkenyl group having a $C_{1-36}$ carbon atom content, with or without the hydrogen atom(s) being substituted with fluorine atom(s), which is the $R_1$ in formula (I) or (IX) of the phosphoric acid ester of of this invention, are such groups as methyl, ethyl, butyl, hexyl, octyl, decyl, dodecyl, tetradecyl, hexadecyl, octadecyl, docosyl, tetracosyl, triacontyl, 2-ethylhexyl, 2-octyldodecyl, 2-dodecylhexadecyl, 2-tetradecyloctadecyl, monomethyl branched-isostearyl, tridecafluorooctyl, heptadecafluorododecyl, heneicosafluorododecyl, pentacosafluorotetradecyl, nonacosafluorohexadecyl, tritriacontafluorooctadecyl, 2-pentafluoroethylpentafluorohexyl, 2-tridecafluorohexyltridecafluorodecyl, 2-heptadecafluorooctylhepatdecafluorododecyl, 2-heneicosafluorodecylheneicosafluorotetradecyl, 2-pentacosafluorododecylpentacosafluorohexadecyl, 2-nonacosafluorotetradecylnonacosafluorooctadecyl, octenyl, decenyl, dodecenyl, tetradecenyl, hexadecenyl, octadecenyl, docosenyl, tetracosenyl, triacontenyl, ethylphenyl, butylphenyl, hexylphenyl, octylphenyl, nonylphenyl, and the like. Among these, those having a $C_{8-36}$, especially $C_{8-24}$, carbon atom content, are preferable in view of surface activity and self organizing capability. An alkylene group having a $C_{2-3}$ carbon atom content, which is represented by $R_2$, may be ethylene, 1-methylethylene, or propylene. Alkyl groups having a $C_{1-3}$ carbon atom content, which are represented by $R_3$ and $R_4$, include methyl, ethyl, 1-methylethyl, propyl, or the like groups. Given as examples of the groups represented by $R_5$ or $R_6$ of formula (I) or (IX) are hydogen atom, and methyl, 1-methylethyl, 1-methylpropyl, 2-methylpropyl, 2-methylthioethyl, carbamoilmethyl, 2-carbamoilethyl, carboxymethyl, 2-carboxyethyl, 4-aminobutyl, 3-guanidinopropyl, benzyl, hydroxymethyl, 1-hydroxyethyl, 4-hydroxyphenylmethyl, imidazol, indol, and the like groups.

Given as specific groups represnted by $R_7$ and $R_8$ of formula (IX) are hydrogen atom, methyl group, ethyl group, propyl group, and the like. Among these, hydrogen atom and methyl group are preferable.

The phosphoric acid ester (I) of this invention can be prepared by a novel process represented, for example, by the following reaction scheme:

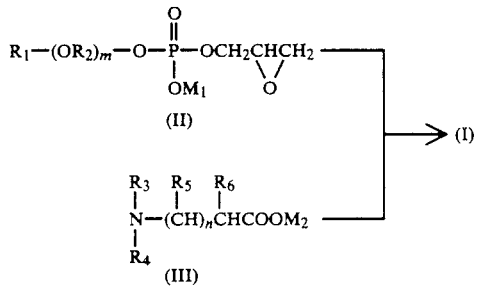

wherein $M_1$ and $M_2$ independently represent a hydrogen atom, an alkali metal, an alkali earth metal, an ammonium group, an alkyl amine group, or an alkanol amine group, $R_1$–$R_6$, m, and n have the same meanings as previously defined.

The phosphoric acid ester (IX) of this invention can be prepared by a novel process represented, for example, by the following reaction scheme:

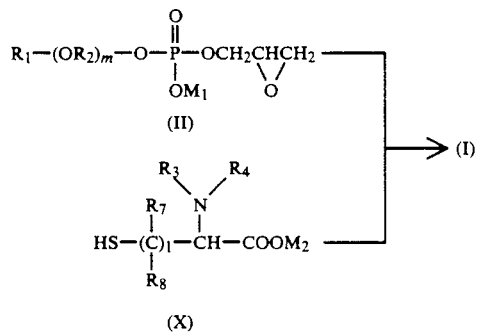

wherein $R_1$–$R_4$, $R_7$, $R_8$, m, l, $M_1$ and $M_2$ have the same meanings as previously defined.

The salt of phosphoric acid ester of formula (II) used in the process of this invention may be the one prepared by any method. One example is the compound prepared by the process proposed by some of the inventors of the present invention, which comprises reacting a high purity monoalkali metal salt of phosphoric acid ester and epihalohydrin, followed by ring-closing of the resulting compound with an alkali. The salt of phosphoric acid ester of formula (II) can be industrially prepared by this process with ease.

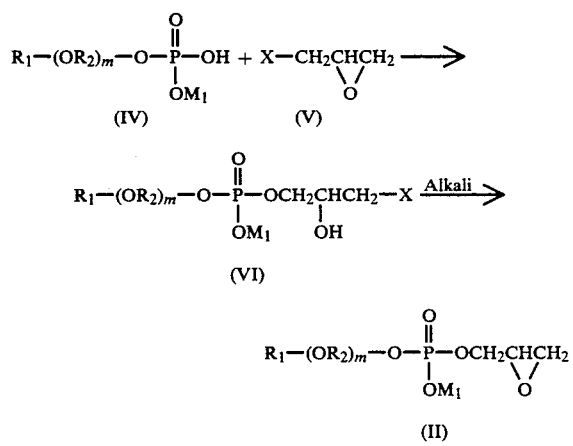

wherein X represents a halogen atom, and $R_1$, $R_2$, $M_1$, and m have the same meanings as previously defined.

Specifically, the compound of formula (II) is easily prepared by reacting a monoalkali metal salt of phosphoric acid ester of formula (IV) with epihalohydrin of formula (V) to produce the compound of formula (VI), and by subjecting this compound to ring-closing reaction in the presence of an alkali.

Examples of amino acids represented by formula (III) include glycine, N-methylglycine, N,N-dimethylglycine, alanine, β-alanine, valine, leucine, isoleucine, γ-aminobutyric acid, ε-aminocaproic acid, proline, phenylglycine, phenylalanine, tryptophan, histidine, methionine, cystine, serine, tyrosine, asparagine, glutamine, aspartic acid, glutamic acid, lysine, arginine, citrulline, ornithine, and the like. Given as an examples of amino acid represented by formula (X) are cysteine, homocysteine, penicillamine, and the like. These amino acid may be either an optically active isomer or a racemic isomer, and may be used either as they are or as salts. The types of the salts employed are alkali metal salt, ammonium salt, alkyl amine salt, or alkanol amine salt.

In the above reaction, 1-10 mol, preferably 1-5 mol, of the amino acid (III) or (IX) is reacted per 1 mol of the phosphoric acid ester (II).

An inert, polar solvent such as, for example, water, methyl alcohol, ethyl alcohol, 2-propanol, or the like, is desirably used as a solvent in the reaction. These solvent may be used either independently or in combination with one or more of the other solvent.

The reaction is carried out at a temperature of 30°–100° C., and preferably of 60°–90° C.

Beside the target compound of formula (I) or (IX), unreacted amino acid is contained in the reaction mixture depending on the molar ratio of the raw materials used. The reaction product thus prepared can be used as is depending on the use intended. It is possible, however, to refine the product to make it into a high purity product. The refining can be performed by means of crystallization, dialysis, or fractionation by silica gel chromatography or high performance liquid chromatography. For instance, sodium dodecyl 2-hydroxy-3-N-carboxymethyl-N,N-dimethylammoniopropyl phosphate [the compound of formula (I), wherein $R_1$ is $C_{12}H_{25}$, $R_3$ and $R_4$ are $CH_3$, $R_5$ and $R_6$ are hydrogens, M is sodium, and n and m are zero] is prepared by reacting sodium dodecyl glycidyl phosphate and N,N-dimethyl glycine in a mixed solvent of water and ethyl alcohol, and adding to the reaction mixture a large amount of acetone to crystallize sodium dodecyl 2-hydroxy-3-N-carboxymethyl-N,N-dimethylammoniopropyl phosphate at a high purity.

When the dissociation constant is taken into account, the phosphoric acid ester represented by formula (I) takes the following structure at neutral conditions:

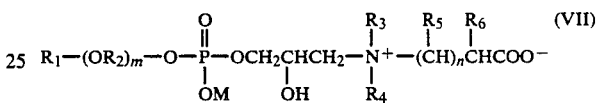

wherein $R_1$–$R_6$, M, m, and n have the same meaning as defined above.

Similarly, when the dissociation constant is taken into account, the phosphoric acid ester represented by formula (IX) takes the following structure at neutral conditions:

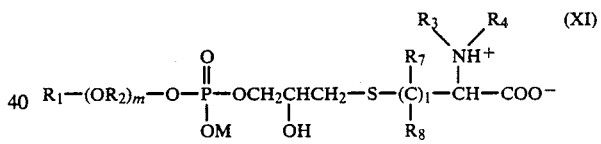

wherein $R_1$–$R_4$, $R_7$, $R_8$, m, l, M and have the same meanings as previously defined.

Depending on the reaction conditions, the phosphoric acid ester of formula (II) and amino acid of formula (III) may produce, beside the phosphoric acid ester of formula (I), a small amount of the phosphoric acid ester of the following formula (VIII):

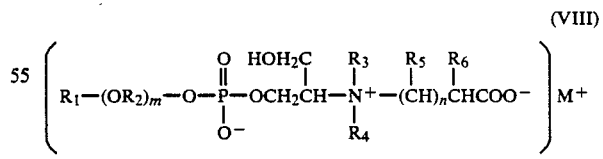

wherein $R_1$–$R_6$, M, m, and n have the same meanings as previously defined.

Also, depending on the reaction conditions, the phosphoric acid ester of formula (II) and amino acid of formula (III) having a mercapto group may produce, beside the phosphoric acid ester of formula (IX), a small amount of the phosphoric acid ester of the following formula (XII):

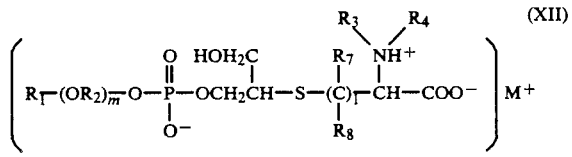

wherein $R_1-R_4$, $R_7$, $R_8$, m, l, M and have the same meanings as previously defined.

Since the phosphoric acid esters (I) and (IX) of this invention has outstanding surface activity and good foaming capability, and imparts only extremely low irritation to the skin, it can produce an excellent detergent composition when formulated into it.

Although there is no specific limitation to the amount of the phosphoric acid ester (I) or (IX) to be formulated into the detergent composition of this invention the desirable range is 1-80% by weight, with particularly desirable range being 5-70% by weight.

Other anionic and/or nonionic surface active agents may be used together with the phosphoric acid ester (I) or (IX) in the detergent composition of this invention without problem. In addition, other components, including water, solvents, coloring agents, inorganic and/or organic salts, viscosity adjusting agents, perfumes, biocidal agents, antiphlogistics, chelating agents, foaming promoting agents, antiseptics, moisturizing agents, and the like, may be formulated into the detergent composition of this invention, to the extent that the effect of the invention may not be impaired.

Since the phosphoric acid esters (I) and (IX) of this invention have outstanding surface activity and good foaming capability, and imparts only extremely low irritation to the skin, the detergent composition into which this compound is formulated is particularly useful as, for example, shampoo, baby shampoo, body shampoo, and the like.

Other features of the invention will become apparent in the course of the following description of the exemplary embodiments which are given for illustration of the invention and are not intended to be limiting thereof.

EXAMPLES

Example 1

N-methylglycine, 10.0 g (0.112 mol), was charged into a reaction vessel, into which 100 ml of water was added and the mixture was stirred The temperature was raised to 70° C. and the mixture was homogenized. Then, while maintaining this temperature, a solution of 38.7 g (0.112 mol) of sodium dodecylglicidyl phosphate in 1,000 ml of ethanol was added dropwise, followed by stirring for 6 hours. The reaction was terminated, when the analysis by high performance liquid chromatography (HPLC) indicated extinction of the peak for the raw material and appearance of the peak for the new product. Upon completion of the reaction, the solvent was evaporated in vacuo to produce 48.2 g of sodium dodecyl 2-hydroxy-3-N-carboxymethyl-N-methylammoniopropyl phosphate in a form of white solid at a yield of 99.1%.

$^1$H —NMR:δ (ppm), FIG. 1
0.8 (t, 3H, -P-OCH$_2$CH$_2$(CH$_2$)$_9$CH$_3$)
1.3 (broad S, 18H, -P-OCH$_2$CH$_2$(CH$_2$)$_9$CH$_3$)
1.6 (broad, 2H, -P-OCH$_2$CH$_2$(CH$_2$)$_9$CH$_3$)

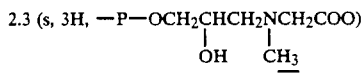

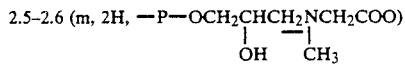

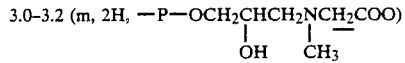

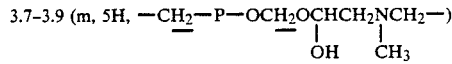

$^{13}$C - NMR:

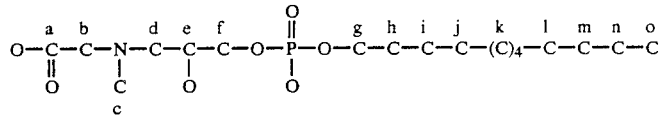

δ(ppm) o;14.1, n;22.7, i;25.8, j;29.8 k;29.9, h;30.5, m;32.0, c;43.0 b;59.8, d;62.0, g;66.3, e;67.8, f;68.0, a;178.6

Figure 2:
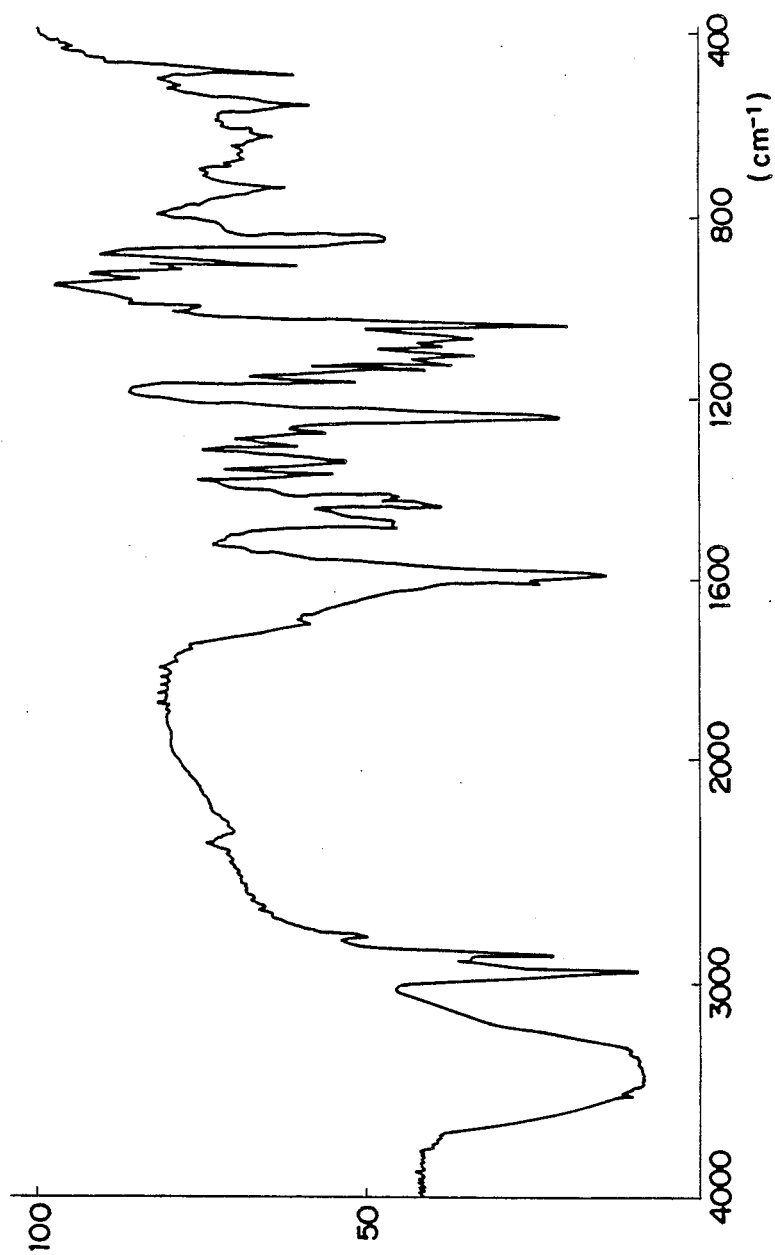
FIG. 2 is a drawing showing IR Spectrum of sodium dodecyl 2-hydroxy-3-N-carboxymethyl-N-methylammoniopropyl phosphate prepared in Example 1.

IR (KBr Tablet Method): FIG. 2

| | Elemental Analysis | | | | |
|---|---|---|---|---|---|
| | C (%) | H (%) | P (%) | N (%) | Na (%) |
| Found | 49.04 | 8.51 | 6.9 | 3.11 | 5.0 |
| Calculated | 49.88 | 8.60 | 7.1 | 3.23 | 5.3 |

Test Example 1

Foaming capability (Reverse Stirring Method*) and Krafft point of sodium dodecyl 2-hydroxy-3-N-carboxymethyl-N-methylammoniopropyl phosphate prepared in Example 1 were measured to obtain the result as shown in Table 1 below. Comparison of these figures with those of sodium dodecyl phosphate indicates that the former has almost the same foaming capability with and extremely lower Krafft point than the latter.

* The conditions of the reverse stirring
Temperature: 40° C.

Rotation speed: 1,000 rpm
Stirring time: 30 sec. (reversed at every 5 sec.)
Measurement: performed after the test sample was left for 10 sec.

TABLE 1

|  | Foaming capability (Foam volume ml) | Krafft point (°C.) |
| --- | --- | --- |
| 1-sodium dodecyl phosphate | 260 | 32 |
| sodium dodecyl 2,3-dihydroxypropyl phosphate | 240 | <0 |
| sodium dodecyl 2-hydroxy-3-N-carboxymethyl-N-methyl-ammoniopropyl phosphate | 250 | <0 |

Example 2

Cysteine, 10.0 g (0.0825 mol), was charged into a reaction vessel, into which 100 ml of water was added and the mixture was stirred. Its temperature was raised to 70° C. and the mixture was homogenized. Then, while maintaining the temperature an ethanol solution of 750 g (0.0825 mol) of sodium dodecyl glycidyl phosphate, which was prepared by the reaction of 31.4 g (0.0825 mol) of sodium dodecyl 2-hydroxy-3-chloropropyl phosphate and sodium hydroxide in ethanol followed by purification by desalting, was added dropwise, and stirring was continued for further 6 hours. The reaction was terminated, when the analysis by HPLC indicated extinction of the peak for the raw material and appearance of the peak for the new product. Upon completion of the reaction, the solvent was evaporated in vacuo to produce 38.1 g of sodium 2-hydroxy-3-[(2-amino-2-carboxy)ethylthio]propyl phosphate at a yield of 99.2%.

Elemental Analysis:

|  | Elemental Analysis | | | | | |
| --- | --- | --- | --- | --- | --- | --- |
|  | C (%) | H (%) | P (%) | N (%) | Na (%) | S (%) |
| Found | 45.59 | 7.95 | 6.6 | 2.88 | 4.8 | 6.70 |
| Calculated | 46.44 | 8.01 | 6.7 | 3.01 | 4.9 | 6.89 |

Example 3

N,N-dimethylglycine, 10.0 g (0.0970 mol) was charged into a reaction vessel, into which 100 ml of water was added and the mixture was stirred. Its temperature was raised to 70° C. and the mixture was homogenized. Then, while maintaining the temperature, a solution of 38.9 g (0.0970 mol) of sodium 2-hexyldecyl glycidyl phosphate in 750 ml of ethanol was added dropwise, followed by stirring for 6 hours. The reaction was terminated, when the analysis by HPLC indicated extinction of the peak for the raw material and appearance of the peak for the new product. Upon completion of the reaction, the solvent was evaporated in vacuo to produce 48.3 g of sodium 2-hexyldecyl 2-hydroxy-3-N-carboxymethyl-N,N-dimethylammoniopropyl phosphate at a yield of 98.9%.

|  | Elemental Analysis | | | | |
| --- | --- | --- | --- | --- | --- |
|  | C (%) | H (%) | P (%) | N (%) | Na (%) |
| Found | 54.11 | 9.32 | 6.1 | 2.68 | 4.5 |
| Calculated | 54.86 | 9.41 | 6.2 | 2.78 | 4.6 |

Example 4

β-Alanine, 30.0 g (0.337 mol), was charged into a reaction vessel, into which 100 ml of water was added and the mixture was stirred. Its temperature was raised to 70° C. and the mixture was homogenized. Then, while maintaining the temperature, an ethanol solution of 750 g (0.112 mol) of sodium butyl glycidyl phosphate, which was prepared by the reaction of 30.2 g (0.112 mol) of sodium 2-hydroxy-3-chloropropyl phosphate and sodium hydroxide in ethanol, followed by purification by desalting, was added dropwise, and stirring was continued for further 6 hours. The reaction was terminated, when the analysis by HPLC indicated extinction of the peak for the raw material and appearance of the peak for the new product. Upon completion of the reaction, the product was collected by fractionation by HPLC. The solvent was evaporated in vacuo to produce 35.8 g of sodium 2-hydroxy-3-N-carboxyethylammoniopropyl phosphate at a yield of 99.3%.

|  | Elemental Analysis | | | | |
| --- | --- | --- | --- | --- | --- |
|  | C (%) | H (%) | P (%) | N (%) | Na (%) |
| Found | 36.50 | 6.1 | 9.5 | 4.26 | 7.1 |
| Calculated | 37.39 | 6.71 | 9.6 | 4.36 | 7.2 |

Example 5

Serine, 10.0 g (0.0952 mol), was charged into a reaction vessel, into which 95.2 ml (0.0952 mol) of 1 N aqueous solution of sodium hydroxide was added and the mixture was stirred Its temperature was raised to 70° C. and the mixture was homogenized. Then, while maintaining the temperature, 45.3 g (0.0952 mol) of sodium trioxyethylenedodecylether glycidyl phosphate in 750 ml of ethanol was added dropwise, and stirring was continued for 6 hours. The reaction was terminated, when the analysis by HPLC indicated extinction of the peak for the raw material and appearance of the peak for the new product. Upon completion of the reaction, the reaction mixture was neutralized by the addition of 95.2 ml (0.0952 mol) of 1 N hydrochloric acid, and dialyzed for desalting. The solvent was evaporated in vacuo to produce 54.3 g of sodium trioxyethylenedodecylether 2-hydroxy-3-N-(1-hydroxymethyl-carboxymethylammoniopropyl phosphate at a yield of 98.1%.

|  | Elemental Analysis | | | | |
| --- | --- | --- | --- | --- | --- |
|  | C (%) | H (%) | P (%) | N (%) | Na (%) |
| Found | 49.11 | 8.35 | 5.2 | 2.30 | 3.8 |
| Calculated | 49.56 | 8.49 | 5.3 | 2.41 | 4.0 |

Example 6

Glycine, 30.0 g (0.400 mol), was charged into a reaction vessel, into which 100 ml of water was added and the mixture was stirred The mixture was heated to 70° C. and homogenized. Then, while maintaining the temperature, a solution of 56.8 g (0.133 mol) of sodium octadecenyl glycidyl phosphate in 750 ml of ethanol was added dropwise, and stirring was continued for 6 hours. The reaction was terminated, when the analysis by HPLC indicated extinction of the peak for the raw material and appearance of the peak for the new product. Upon completion of the reaction, the reaction products were fractionated by HPLC and the solvent was evaporated in vacuo to produce 65.3 g of sodium octadecyl 2-hydroxy-3-N-carboxymethylammoniopropyl phosphate at a yield of 97.7%.

|  | Elemental Analysis | | | | |
| --- | --- | --- | --- | --- | --- |
|  | C (%) | H (%) | P (%) | N (%) | Na (%) |
| Found | 54.82 | 8.95 | 6.1 | 2.56 | 4.5 |
| Calculated | 55.08 | 9.04 | 6.2 | 2.79 | 4.6 |

Example 7

Alanine, 10.0 g (0.112 mol), was charged into a reaction vessel, into which 112 ml of 1 N aqueous solution of sodium hydroxide was added and the mixture was stirred. The mixture was heated to 70° C. and homogenized. Then, while maintaining the temperature, a solution of 73.9 g (0.112 mol) of sodium heptadecafluorodecyl glycidyl phosphate in 750 ml of ethanol was added dropwise, and stirring was continued for 6 hours. The reaction was terminated, when the analysis by HPLC indicated extinction of the peak for the raw material and appearance of the peak for the new product. Upon completion of the reaction, the reaction mixture was neutralized by the addition of 112 ml (0.112 mol) of 1 N hydrochloric acid, and dialyzed for desalting. The solvent was evaporated in vacuo to produce 79.0 g of sodium heptadecafluorodecyl 2-hydroxy-3-N-(1-methyl)carboxymethylammoniopropyl phosphate at a yield of 99.0%.

|  | Elemental Analysis | | | | | |
| --- | --- | --- | --- | --- | --- | --- |
|  | C (%) | H (%) | F (%) | P (%) | N (%) | Na (%) |
| Found | 26.66 | 2.17 | 44 | 4.3 | 1.88 | 3.1 |
| Calculated | 27.02 | 2.27 | 45 | 4.4 | 1.97 | 3.2 |

Example 8

Methionine, 10.0 g (0.0670 mol), was charged into a reaction vessel, into which 100 ml of water was added and the mixture was stirred. The mixture was heated to 70° C. and homogenized. Then, while maintaining the temperature, 750 g (0.0670 mol) of an ethanol solution of sodium nonylphenyl glycidly phosphate, which was prepared by the reaction of 27.8 g (0.0670 mol) of sodium nonylphenyl 2-hydroxy-3-chloropropvl phosphate and sodium hydroxide in ethanol, was added dropwise, and stirring was continued for 6 hours. The reaction was terminated, when the analysis by HPLC indicated extinction of the peak for the raw material and appearance of the peak for the new product. Upon completion of the reaction, the reaction products were fractionated by HPLC and the solvent was evaporated in vacuo to produce 32.7 g of sodium nonylphenyl 2-hydroxy-3-N(1-mercaptomethyl)carboxymethylammoniopropyl phosphate at a yield of 97.7%.

|  | Elemental Analysis | | | | | |
| --- | --- | --- | --- | --- | --- | --- |
|  | C (%) | H (%) | P (%) | N (%) | Na (%) | S (%) |
| Found | 50.20 | 7.00 | 6.1 | 2.75 | 4.3 | 6.33 |
| Calculated | 50.49 | 7.06 | 6.2 | 2.80 | 4.6 | 6.42 |

Example 9

A detergent composition was prepared, which has the formulation of Table 2 below and into which sodium dodecyl 2-hydroxy-3-N-carboxymethyl-N-methylammoniopropyl phosphate prepared in Example 1 was formulated together with other components. This detergent composition (body shampoo) gave no irritation to the skin during use, provided a fresh feeling with no slipperiness after use, and retained a moisturizing feel after washing.

TABLE 2

| Detergent Formulation (Body Shampoo) | |
| --- | --- |
| Sodium dodecyl 2-hydroxy-3-N-carboxymethyl-N-methylammoniopropyl phosphate | 25.0 wt % |
| Triethanolamine laurate | 5.0 |
| Lauryldimethylamine oxide | 4.0 |
| Cationized cellulose | 0.1 |
| Glycerin | 5.0 |
| Sorbitol | 2.0 |
| Perfumes, Antiseptics | Appropriate amount |
| Purified water | Balance |

Example 10

A shampoo composition was prepared, which has the formulation of Table 3 below and into which sodium dodecyl 2-hydroxy-3-N-carboxymethyl-N-methylammoniopropyl phosphate prepared in Example 1 was formulated together with other components. The composition was an excellent shampoo producing fine foam and providing a smooth feeling to the hair with no irritation.

TABLE 3

| Detergent Formulation (Shampoo) | |
| --- | --- |
| Sodium dodecyl 2-hydroxy-3-N-carboxymethyl-N-methylammoniopropyl phosphate | 15.0 wt % |
| Coconut oil diethanolamide | 3.0 |
| Dodecyldimethylamino acetate betaine | 3.0 |
| Disodium ethylenediamine tetraacetate | 0.1 |
| Citric acid | 0.1 |
| Purified water | Balance |

Example 11

Homocystein, 10.0 g (0.0740 mol), was charged into a reaction vessel, into which 100 ml of water was added and the mixture was stirred. The temperature was raised to 70° C. and the mixture was homogenized. Then, while maintaining the temperature at 70° C., a solution of 29.6 g (0.0740 mol) of sodium hexadecyl glycidyl phosphate in 750 ml of ethanol was added dropwise, followed by stirring for 6 hours. The reaction was terminated when the analysis by HPLC indicated extinction of the peak for the raw material and appearance of the peak for the new product.

Upon completion of the reaction, the solvent was evaporated in vacuo to produce 37.3 g of sodium hexadecyl 2-hydroxy-3-[(amino-3-carboxy)propylthio]propyl phosphate at a yield of 94.1%.

|  | Elemental Analysis | | | | | |
| --- | --- | --- | --- | --- | --- | --- |
|  | C (%) | H (%) | P (%) | N (%) | Na (%) | S (%) |
| Found | 51.73 | 8.92 | 5.7 | 2.69 | 4.4 | 5.93 |

-continued

| | Elemental Analysis | | | | | |
|---|---|---|---|---|---|---|
| | C (%) | H (%) | P (%) | N (%) | Na (%) | S (%) |
| Calculated | 51.58 | 8.84 | 5.8 | 2.61 | 4.3 | 5.99 |

Example 12

Penicillamine, 10.0 g (0.0670 mol), was charged into a reaction vessel, into which 100 ml of water was added and the mixture was stirred. The temperature was raised to 70° C. and the mixture was homogenized. Then, while maintaining the temperature at 70° C., a solution of 42.0 g (0.0670 mol) of sodium 2-tetradecyloctadecyl glycidyl phosphate in 750 ml of ethanol was added dropwise, followed by stirring for 6 hours. The reaction was terminated when the analysis by HPLC indicated extinction of the peak for the raw material and appearance of the peak for the new product.

Upon completion of the reaction, the solvent was evaporated in vacuo to produce 49.7 g of sodium 2-tetradecyloctadecyl 2-hydroxy-3-[(2-amino-2-carboxy-1,1-dimethyl)ethylthio]propyl phosphate at a yield of 95.8%.

| | Elemental Analysis | | | | | |
|---|---|---|---|---|---|---|
| | C (%) | H (%) | P (%) | N (%) | Na (%) | S (%) |
| Found | 62.05 | 10.31 | 3.9 | 1.88 | 3.1 | 4.12 |
| Calculated | 62.06 | 10.55 | 4.0 | 1.81 | 3.0 | 4.14 |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. A phosphoric acid ester represented by the following formula (I):

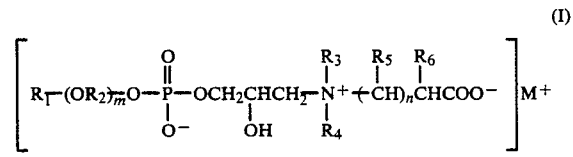

wherein $R_1$ represents a linear or branched, alkyl or alkenyl group having a $C_{8-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content, $R_3$ and $R_4$ independently denote a hydrogen atom or an alkyl group having a $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s) excepting for a mercapto group, m is an integer of 0-30, n is an integer of 0-5, M is a hydrogen atom, an alkali metal, an alkali earth metal, an ammonium group, an alkyl amine group, or an alkanol amine group.

2. A detergent composition comprising a phosphoric acid ester represented by the following formula (I):

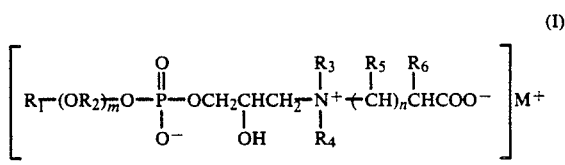

wherein $R_1$ represents a linear or branched, alkyl or alkenyl group having a $C_{8-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content, $R_3$ and $R_4$ independently denote a hydrogen atom or an alkyl group having $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s), excepting for a mercapto group, m is an integer of 0-30, n is an integer of 0-5, M is a hydrogen atom, an alkali metal, an alkali earth metal, an ammonium group, an alkyl amine group, or an alkanol amine group and at least one member selected from the group consisting of other anionic or nonionic surface active agents, water, nonaqueous solvents, coloring agents, inorganic salts, organic salts, viscosity adjusting agents, perfumes, biocidal agents, chelating agents, forming promoting agents, antiseptics, and moisturizing agents.

3. A detergent composition comprising a phosphoric acid ester represented by the following formula

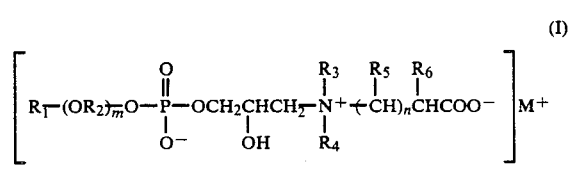

wherein $R_1$ represents a linear or branched, alkyl or alkenyl group having a $C_{8-36}$ carbon atom content, with or without the hydrogen atom(s) being substituted with fluorine atom(s), or a phenyl group with substituted linear or branched alkyl group(s) having a $C_{1-15}$ carbon atom content, $R_2$ represents an alkylene group having a $C_{2-3}$ carbon atom content , $R_3$ and $R_4$ independently denote a hydrogen atom or an alkyl group having a $C_{1-3}$ carbon atom content, $R_5$ and $R_6$ independently denote a hydrogen atom, or an alkyl, alkenyl, or phenyl group with or without the hydrogen atom(s) being substituted with group(s) containing hetero atom(s), excepting for a mercapto group, m is an integer of 0-30, n is an integer of 0-5, M is a hydrogen atom, an alkali metal, an alkali earth metal, an ammonium group, an alkyl amine group, or an alkanol amine group and at least one member selected from the group consisting of other anionic or nonionic surface active agents, water, nonaqueous solvents, coloring agents, inorganic salts, organic salts, viscosity adjusting agents, perfumes, biocidal agents, antiphlogistics, chelating agents, foaming promoting agents, antiseptics, and moisturizing agents.

* * * * *